United States Patent [19]
Slesarev

[11] Patent Number: 5,834,435
[45] Date of Patent: Nov. 10, 1998

[54] INHIBITION OF TNF-α PLEIOTROPIC AND CYTOTOXIC EFFECTS

[76] Inventor: Vladimir I. Slesarev, 20 Colebrook La., Conroe, Tex. 77304

[21] Appl. No.: 757,477

[22] Filed: Nov. 27, 1996

[51] Int. Cl.[6] .................................................. A61K 38/05
[52] U.S. Cl. ................................. 514/19; 514/8; 514/16; 514/921; 514/885; 530/322
[58] Field of Search .................................. 514/19, 8, 16, 514/921, 885; 530/322

[56] References Cited

U.S. PATENT DOCUMENTS

| | | | |
|---|---|---|---|
| 4,395,399 | 7/1983 | Ovchinnikov et al. | 424/177 |
| 4,698,330 | 10/1987 | Krueger et al. | 514/19 |
| 5,506,204 | 4/1996 | Aston | 514/8 |
| 5,534,492 | 7/1996 | Aston et al. | 514/8 |
| 5,594,106 | 1/1997 | Black et al. | 530/331 |
| 5,605,690 | 2/1997 | Jacobs et al. | 424/134.1 |
| 5,629,285 | 5/1997 | Black et al. | 514/2 |

OTHER PUBLICATIONS

Beutler et al., Ann. Rev.Immunol. 7:625–655, 1989.
Vassalli, Ann. Rev.Immunol.10:411–452, 1992.
Adeleye et al., APMIS 102(2):145–152, 1994.
Glazier, et al; Intravesical Recombinant TNF . . . ; Journal of Urology, vol. 154, 66–68, Jun. 1995.
Hiroshi, N, et al., TNF–60 Treatment Journal of Cerebral Blood Flow and Metabolism 17:483–190 (1997).
TNF; The Good, The Bad, and potentially Very effective; Barbara, J.A. et al.; Immunology and Cell Biology 74:434–443 (1996).
Kuppen, PJK et al, Liver & Tumor tissue Conc . . . British J. of Cancer; (1997) 75(10) 1497–1500.
Palache, A.M., et al; Vaccine, vol. 14, No. 14, pp. 1327–1330, (1996).
Kusama T., et al; Eur Surg Res 1997; 29:375–381 (1997).
Martin C., et al; Crit Care Med, vol. 25, No. 11: 1813–1819 (1997).
Skerrett, S., et al; The Journal of Infectious Diseases; 176: 1019–28 (1997).
Liaw, C., et al; Acta Oncologica, vol. 36, No. 2 pp. 159–164 (1997).
Endo, S., et al; Butterworth–Heinemann Ltd. 0305–4179/93/020124–04 (1993).
Endo, S., et al; Butterworth–Heinemann Ltd. 0305–4179/92/060486–04 (1992).
Fabian, T., et al; Surgery, 118:63–72 (1995).
Alexander, H., et al; Infection and Immunity, vol. 59, No. 11, pp. 3889–3894 (1991).
Nelson, S., et al; J. Moll Cell Cardiol 27, 223–229 (1995).
Brown, J., et al; Physiological Sciences, vol. 86, pp. 2516–2520 (1989).
Takasuka, N., et al; The American Association of Immunologists, vol. 146, No. 11, 3824–3830 (1991).
Eddy, L., et al; Biochemical and Biophysical Research Communications, vol. 184, No. 2, pp. 1056–1059, (1992).
Rowland, R., et al; American Physiological Society, 0363/6135/97 (1997).
Fuks, B. B., et al; Plenum Publishing Corporation, 0007–4888/91/0007–1006$12.50 (1991).
Tsutsumi, Y., et al; British Journal of Cancer, 71, 963–968 (1995).
Neuzil, K., et al; The American Journal of Medical Sciences, vol. 311, No. 5:201–204 (1996).
Koshiji, M., et al; Clin Exp Immunol; 111:211–218 (1998).
Abraham, E., et al; JAMA, vol. 273, No. 12:934–941 (1995).
Livingston, D., et al; The Journal of Trauma, vol. 29, No. 7:967–971 (1989).
Riche, F., et al; Surgery, 120:801–7 (1996).
Reinhart, K., et al; Crit Care Med, Nov. 24, No. 5:733–742 (1996).
Echtenacher, B., et al; Journal of Inflammation 47:85–89 (1996).
Feldman, M., et al; Journal of Inflammation 47:90–96 (1996).
Rowland, R., et al; Journal of Surgical Research 63, 193–198 (1996).
Nawashiro, H., et al, Care Blood Flow and Met., 17:483–490 (1997).
Rigato, O., et al; Infection 24 (1996) No. 4.
Elkon, K.B., et al; Proc. Natl. Acad. Sci., vol. 94, pp. 9814–9819, Sep. 1997, Immunology.
Hoijer, M.A., et al; Eur Cytokine Netw 1997 Dec; 8(4): 375–381. (abstract only).
Fuks, B.B., Biull Eksp Biol Med 1991 Jul; 112(7): 78–80. (abstract only).
Rakhmilevich, A.L., Antibiot Khimioter 1989 Aug., 34(8): 586–589 (abstract only).
Pimenov, A.A., Vopr Med Khim 1990 Jan.; 36(1):58–60. (abstract only).
Meldrum, D.R., Am J Physiol 1997 Aug.;273(2 Pt 2): H725–H733 (abstract only).
Beech, J.T., et al; Br J Rheumatol 1997 Oct.;36(10): 1129 (abstract only).
Koshiji, M., et al; Clin Exp Immunol 1998 Jan.;111(1):211–218 (abstract only).
Fuks, B.B., et al; Buill Eksp Biol Med 1991 Jul.; 112(7): 78–80 (abstract only).
Rakhmilevich, A.L., Antibiot Khimioter 1989 Nov.; 34(11):836–839. (abstract only).

*Primary Examiner*—Stephen Walsh
*Assistant Examiner*—Eliane Lazar-Wesley
*Attorney, Agent, or Firm*—Michael B. Jolly

[57] ABSTRACT

The pleiotropic effects of TNF alfa in a wide variety of mammalian cell types is decreased and treated by administering glucosaminylmuramyl peptides with D-amino acid residue in a second or third position from the proximal end. New methods for nonspecific oral, vaginal, and topic inhibition is proposed. Inhibition of cytotoxicity of TNF alfa is also achieved.

16 Claims, 11 Drawing Sheets

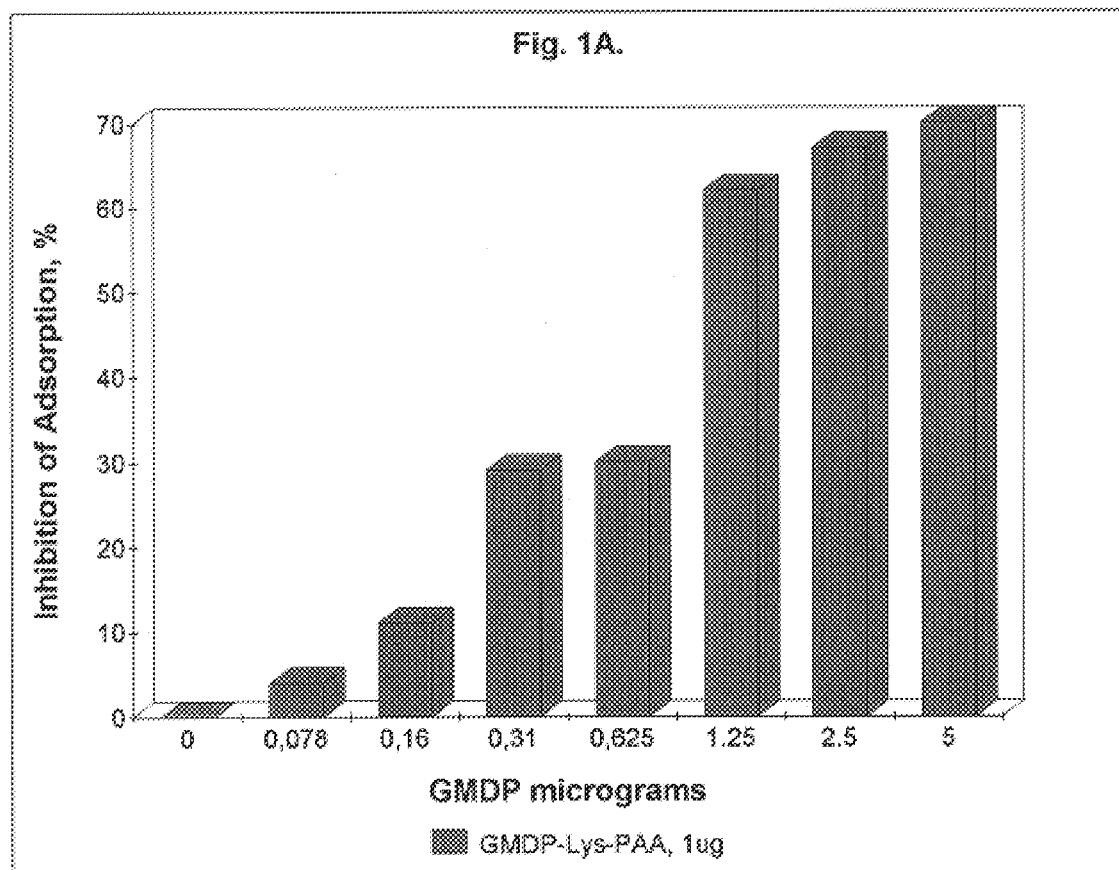

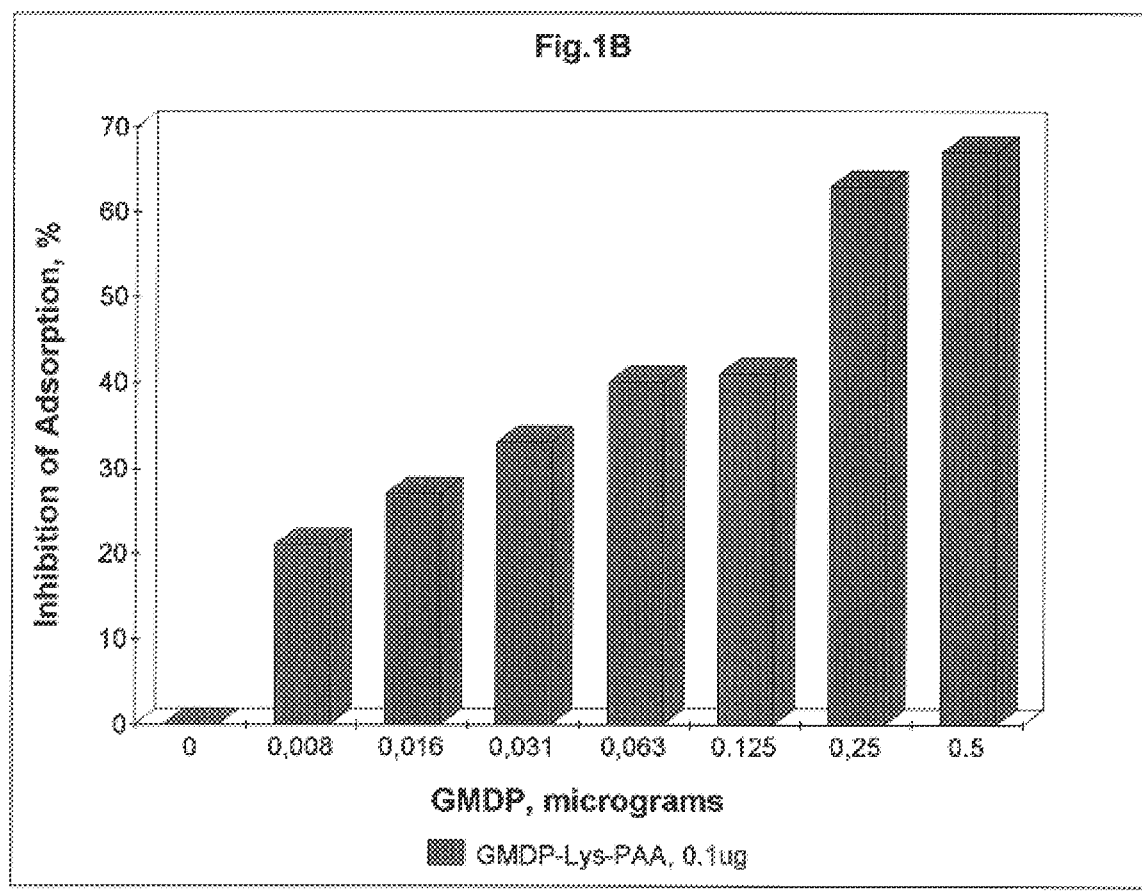

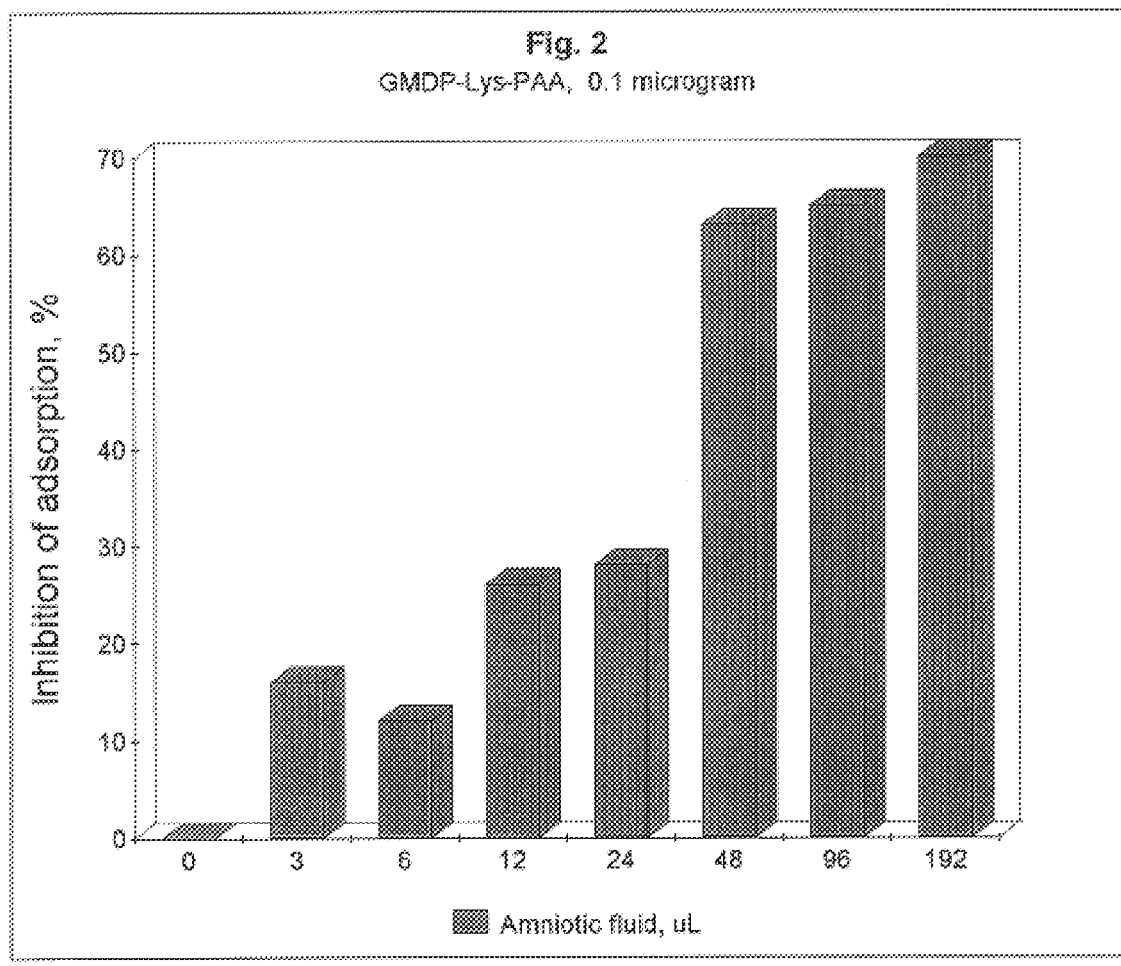

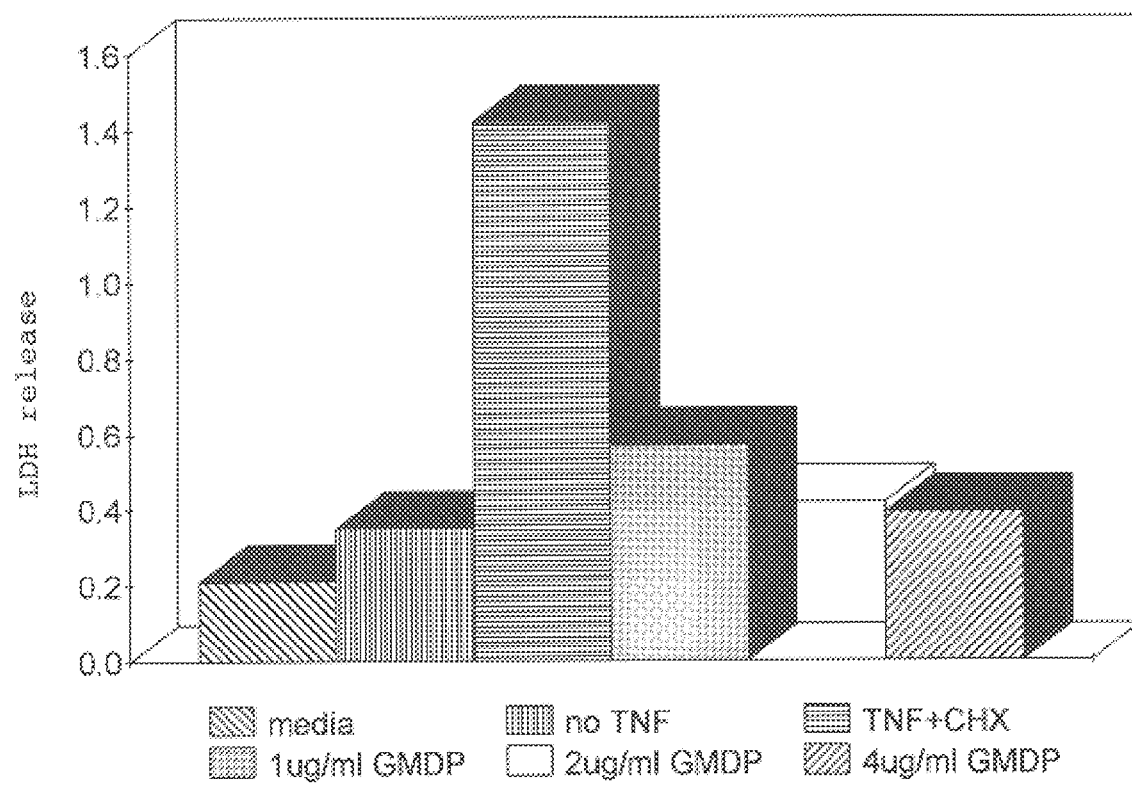

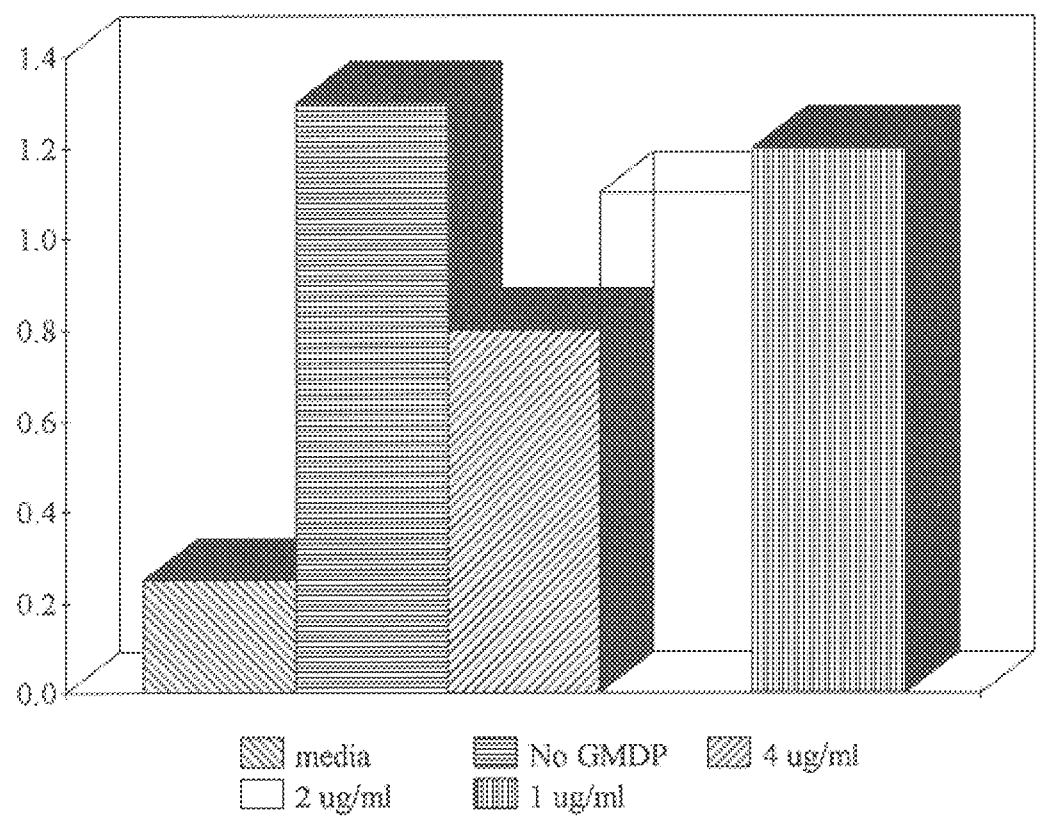

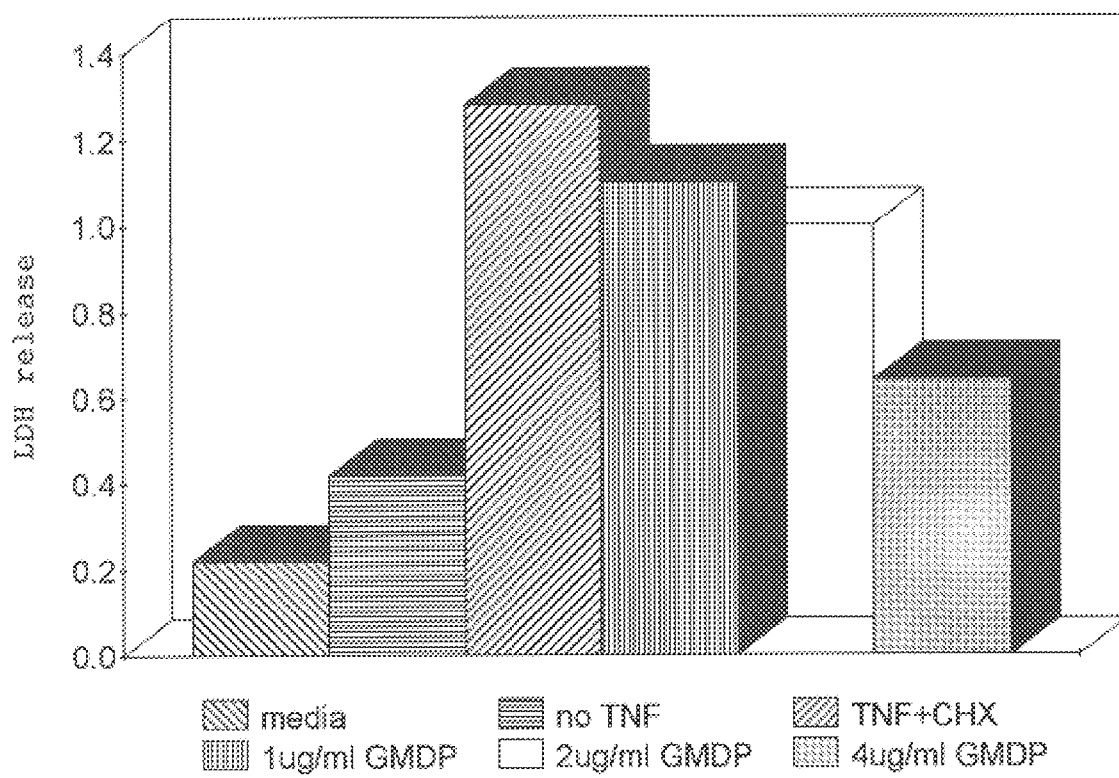

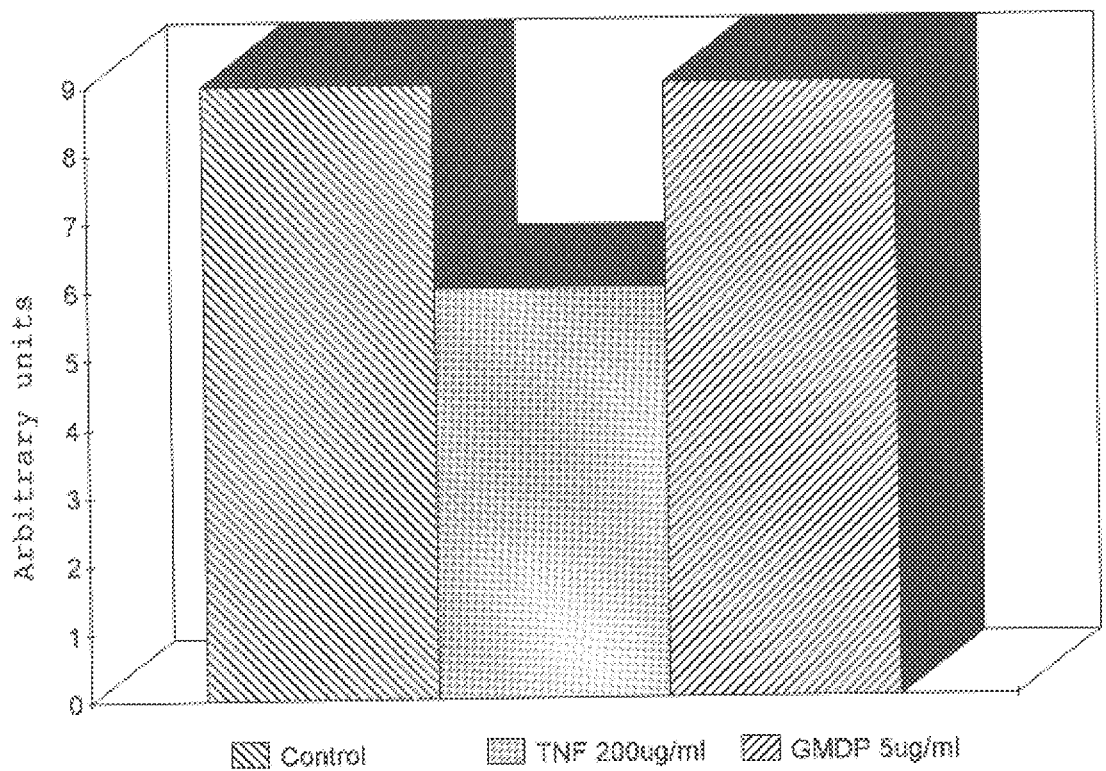

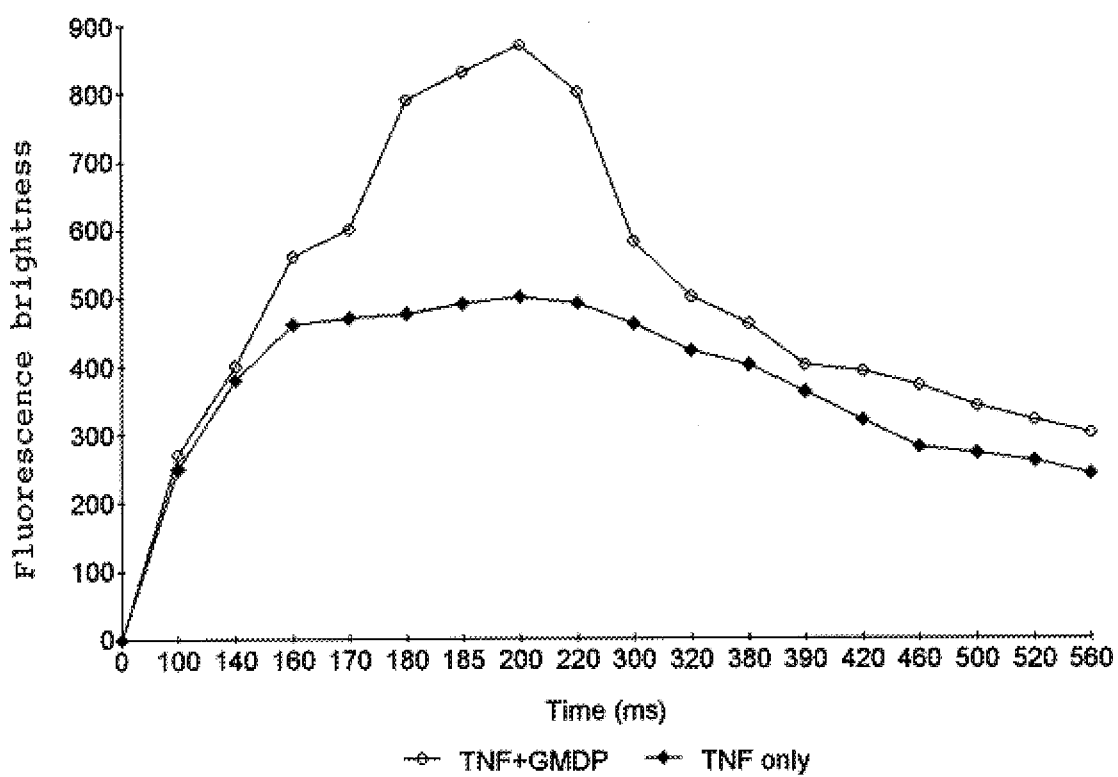

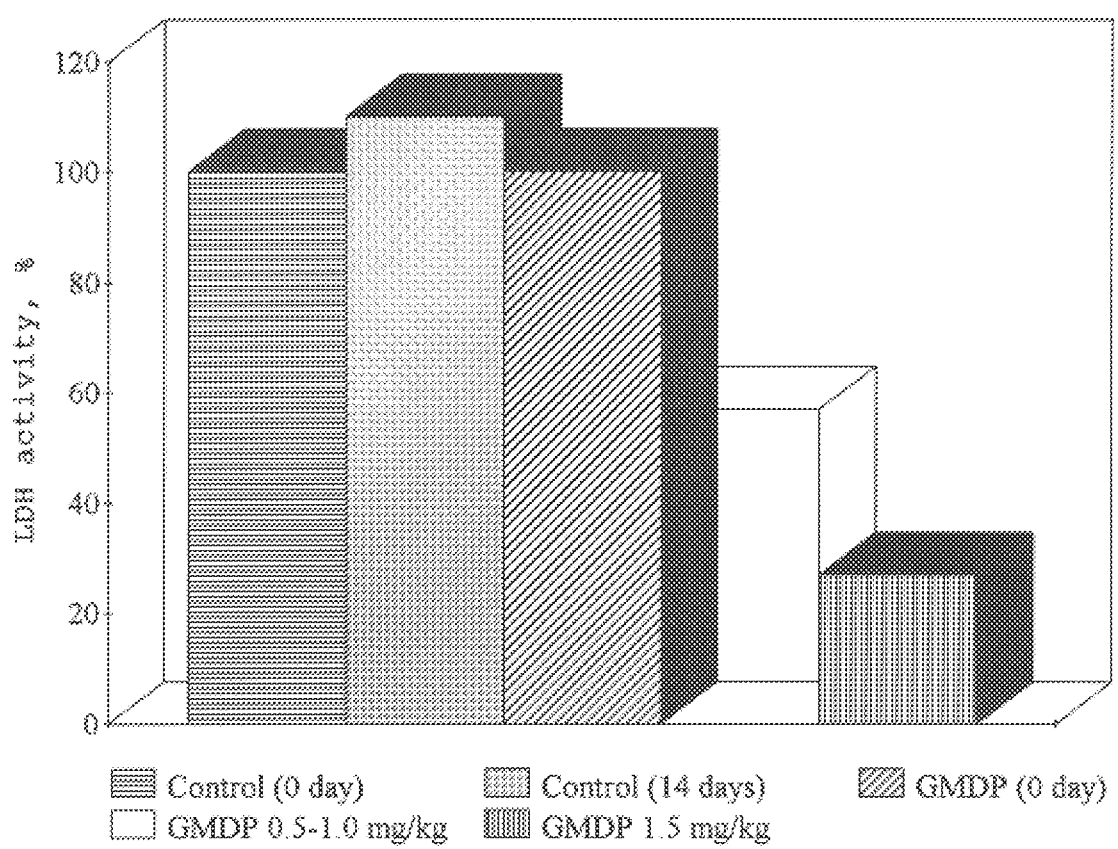

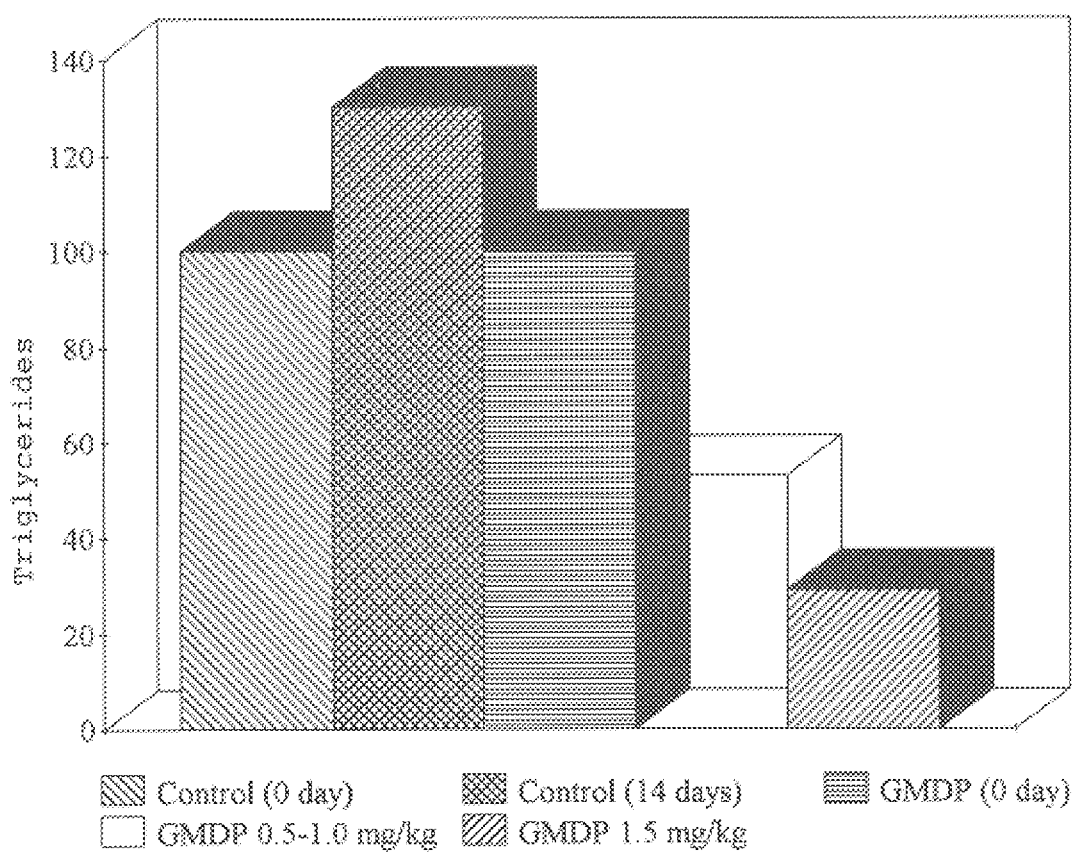

INHIBITION OF TNF-α PLEIOTROPIC AND CYTOTOXIC EFFECTS

BACKGROUND OF THE INVENTION

Tumor necrosis factor-α (TNF-α) was originally discovered as a protein that produced necrotizing effects in certain types of transplantable mouse tumors (Carswell E. A., Old L. J., Kassel R. L., and Williamson B. Proc. Natl. Acad. Sci. 72.:3666–3670, 1975). This factor is considered a main mediator of tumor toxicity, causing cachexia in cancer patients. In the terminate stage of cancer this peptide induces clinical syndrome known as tumor shock, which is characterized by drastic elevation of all 5 lactate dehydrogenase isoenzymes (LDH). TNF-α is also elevated during bum shock and septic shock (Giroir B. P., Horton J. W., White J. D., Am. J.Physiol.,267:H118–H124, 1994).

Subsequent studies have shown that the spectrum of biological activities for TNF-α is not limited to cytotoxic effects but also exerts pleiotropic effects in a wide variety of mammalian cell types, including adult cardiac myocytes (Gulick T. S., Chung M. K., Pieper S. J., Schreiner G. F. Proc. Natl. Acad., Sci. 86:6753–6757, 1986), human placentas (Yelavarthi K., Hunt J. S., Am., J.,Pathol., 143:1131–1141, 1993), dermal fibroblasts (Mauviel A., Heino J., Kahari V. M. J. Invest. Dermatol., 96:243–249, 1993), and pleural mesothelial cells (Owens M. W., Grimes S. R. Am.J.Physiol., 265, L382–L388, 1993). In these cells TNF-α stimulates collagenase and prostaglandin E2 production. This cytokine also exerts multiple effects on lipoprotein lipase in vivo (Semb H., Peterson J., Tavernier J., Olivecrona T., J. Biol. Chem., 262:8390–8394).

In low concentration ($10^{-10}$M), TNF-α is thought to act primarily as a paracrine or autocrine regulator of leukocytes and endothelial cells, and serves to regulate inflammatory responses to microbes and to facilitate tissue repair. In higher concentration ($10^{-8}$M), TNF-α production exceeds the number of TNF receptors in a given tissue, which results in excess TNF-α circulating in the bloodstream. There TNF-α acts as an endocrine hormone that can lead to cachexia (Oloff A., Defeo-Jones D., Boyer M., Cell, 50:555–563, 1987), potentially lethal microvascular coagulation, metabolic acidosis, hemoconcentration, and hypotension (Tracey K. J., Beutler B., Lowry S. F., Science, 234:470–474, 1986).

TNF-α has been shown to exert concentration dependent negative inotropic effects in isolated papillary muscle preparations, as well as in isolated adult cardiac myocytes (Yokoyama T., Vaca L., Rossen R. D., Durante W., Hazarika P., Mann D. L., J. Clin. Invest., 92:2303–2312, 1993).

Recent clinical observations indicate that TNF-α is elaborated in patients with advanced heart failure (Levine B., Kalman J., Mayer L., Fillit H. M., N. Engl. J. Med., 223:236–241.), myosin-induced myocarditis (Smith S. C., Allen P. M. Circ. Res., 70:856–863, 1992.), reperfusion injury, and cardiac allograft rejection. (Arbustini E., Grasso M., Diegoli M. Am.,J. Pathol. 139:709–715),.

Originally, TNF-α elaboration was proposed as a potentially important mechanism for the cachexia, which occurs frequently in this syndrome. Later, increasing evidence suggested that TNF-α may play a much broader pathophysiologic role in heart failure than was originally posited. Many of the clinical hallmarks of heart failure, including left ventricular disfunction, cardiomyopathy and pulmonary edema, can be explained by the known biological effects of TNF-α in humans.

Thus, successful search for the inhibitor of TNF-α signaling pathways would solve the problem of the universal inhibition of the pathophysiological mechanism of diseases.

Recently, the few human inhibitors were isolated from body fluids (Engelman G. L., Novick D., Wallach D., J. Biol. Chem., 265:1531–1536, 1990), (Seckinger P. L., Isaaz S., and Dayer J. M. J.Exp.167:1511–1516, 1988). One of them shows the immunological cross-reactivity with TNF receptor (Seckinger P. L., Zhang J. H., Hauptmann B., Dayer J. M. Proc. Natl. Acad. Sci., 87:51188–5192, 1990)

The first report demonstrating the presence of N-acetyl-muramyl-D-peptide (MDP) in human urine, has been done by Krueger (Krueger, J. M., et al. J. Biol. Chem. 257:1664–1669, 1982). Chemical and physiological properties of this urinary factor resemble those of the sleep factor found in sterile cerebrospinal fluid and in acid/acetone extracts of brains from sleep-deprived animals (Garcia-Arraras and Pappenheimer. J. Neurophysiol. 49:528–533, 1983). In accordance with this discovery, biological compositions for the induction of sleep have been invented [U.S. Pat. No. 4,698,330].

Numerous reports testify to the fact that muramyl peptides induce different mediators of the immune response, such as TNF-α in the macrophage, interleukin-1 (IL-1) and Ia-antigen, both in immunocompetent cells and in brain astrocytes (Vermeulen, M. V., J. Immunol., 139:7–8, 1987). Thus, muramyl peptides maintain the immune status of the organism at a normal level and promote the normal duration of sleep by means of specific mediators whose main function is tightly coupled with the immune system. Similar to some vitamins, muramyl D-peptides are utilized (but not synthesized) by the host organism, and they act as regulators of various physiological systems. It has been suggested that muramyl peptides enter the organism as a result of adsorption of degradation products of normal colibacilli.

Later, GMDP has been identified in human milk. It also has been suggested that glucosaminylmuramyl dipeptides enter the human body after the degradation of probiotic part of the microflora.(Slesarev V. I. et.al., U.S. patent application Ser. No. 08/510,737). This compound was isolated during analysis of the anti-tumor drug, blastolysine, which is a lysozyme cell wall hydrolysate of Lactobacillus Bulgaricus (U.S. Pat. No. 4,395,399). GMDP has been extensively studied in animals, demonstrating adjuvant activity, antitumor activity, low pyrogenicity and hypnogenic effect (Andronova, T., Ivanov, V. Sov. Med. Rev. Immunol. 4:1–63, 1991).

This muramyl dipeptide also has shown to have a modulating effect on TNF-α, lipopolysaccharide (LPS) and MDP, which results in preventing the toxic action of LPS during septic shock (Adeleye T. A., Moreno C., Ivanyi J., Aston R., A.P.M.S.,102:145–152, 1994).

The systemic effect of the probiotics could be clinically important. For example, the subjects who were diagnosed with bacterial vaginosis, a condition in which lactobacilli normally present in vagina are replaced by more virulent species, were also 40% more likely to give birth prematurely (Roush W., Science, 271:139–140, 1996).

How and why the normal probiotic microflora decreases the preterm labor and the toxicity of the pregnancy remains unknown.

BRIEF DESCRIPTION OF THE INVENTION

Applicant suggest that the systemic effect of the human probiotics is caused by an "active ingredient" in lactobacilli, which is a component of the bacterial cell wall, D-peptidoglycan (GMDP). Furthermore, Applicant suggest the GMDP decreases the pleiotropic effects of the TNF-α. This compound is helpful in protecting a wide variety of mammalian cells including, human lung cell, cardiac myocytes, placentas, and lung mesothelial cells from TNF-α cytotoxicity.

Applicant has predicted the presence of GMDP in human amniotic fluid. The protocol for the identification of the bacterial peptidoglycans in human amniotic fluid is described in example 1 of this application. Monoclonal anti-idiotypic antibodies to GMDP have been used in Applicant's technology.

Based on this, one aspect of this invention is to provide novel TNF-α inhibitors available in human body fluids, incorporating in their peptides fragment D-amino-acid in a first, second or third position from the end. Non specificity of the inhibition of the cytotoxicity is achieved by exploiting newly discovered phenomena competitive inhibition of TNF-α signaling pathways including tumor necrosis factor receptor p55(TNFR1) and tumor receptor factor p75 (TNFR2) receptors and their ligands on host cells by D-amino acid containing glucosamynyl muramyl peptides, which results in increased protection of the cells.

Second aspect of this invention comprises vaginal application of this probiotics D-peptidoglycan for the treatment of preterm labor and the treatment of pregnancy toxicity. We suggest that the "active ingredient" in both bifidobacteria and lactobacilli is a component of the bacterial cell wall, GMDP. Furthermore, we suggested that the peptidoglycan GMDP discovered in amniotic fluid are also responsible for decreasing preterm labor and pregnancy toxicity by the vaginal anaerobic microflora. It is also the strong inhibitor of TNF-α killing pathways, which physiologically prevents pleiotropic action of TNF-α on synthesis of prostaglandin E2, coagulation angiopathy, and hypertension.

Based on this assumption, we propose to administer orally and vaginally GMDP a TNF-α inhibitor, which counteracts stimulating effect of the MDP and TNF-α on the synthesis of prostaglandin E2.

Another aspect of the present invention is a system to decrease the pleiotropic effects of TNF-α in a wide variety of mammalian cell types, including cardiac myocytes, placenta, dermal fibroblasts, and pleural mesothelial cells, including the inhibition of the collagenase and prostaglandin E production.

Yet another aspect of the present invention is a treatment of lipids metabolism disturbance, including those caused by TNF-α during tumor shock.

BRIEF DESCRIPTION OF THE DRAWINGS

For further details, reference is made to the discussion which follows, in light of the accompanying drawings, wherein:

FIG. 1 Illustrates the competitive inhibition of the adsorption of E6/1.2 antibody on the adsorbed GMDP-Lys-PAA by GMDP in solution. A, 1 μG GMDP-Lys-PAA per well; B, 0.1 μg GMP-Lys-PAA per well.

FIG. 2 Reports the results of an assay for GMDP in human amniotic fluid. Which is a competitive inhibition of the adsorption of E6/1.2 antibody on the adsorbed GMDP-Lys-PAA by serial dilutions of the amniotic fluid in PBS.

FIG. 3 LDH assay in A549 cells (human lung cancer)

FIG. 4 LDH assay in L929(mouse mammary cancer)

FIG. 5 LDH assay in A431 cells (human lung cancer)

FIG. 6 Illustrates the inhibition of negative inotropic effect of TNF-α on adult cardiac myocytes.

FIG. 7 Typical time-intensity curve for fluorescence brightness in isolated cardiac myocytes.

FIG. 8 LDH activity of the cancer patients.

FIG. 9 Triglycerides concentration in the cancer patients.

DETAILED DESCRIPTION OF THE INVENTION

Figure 10:
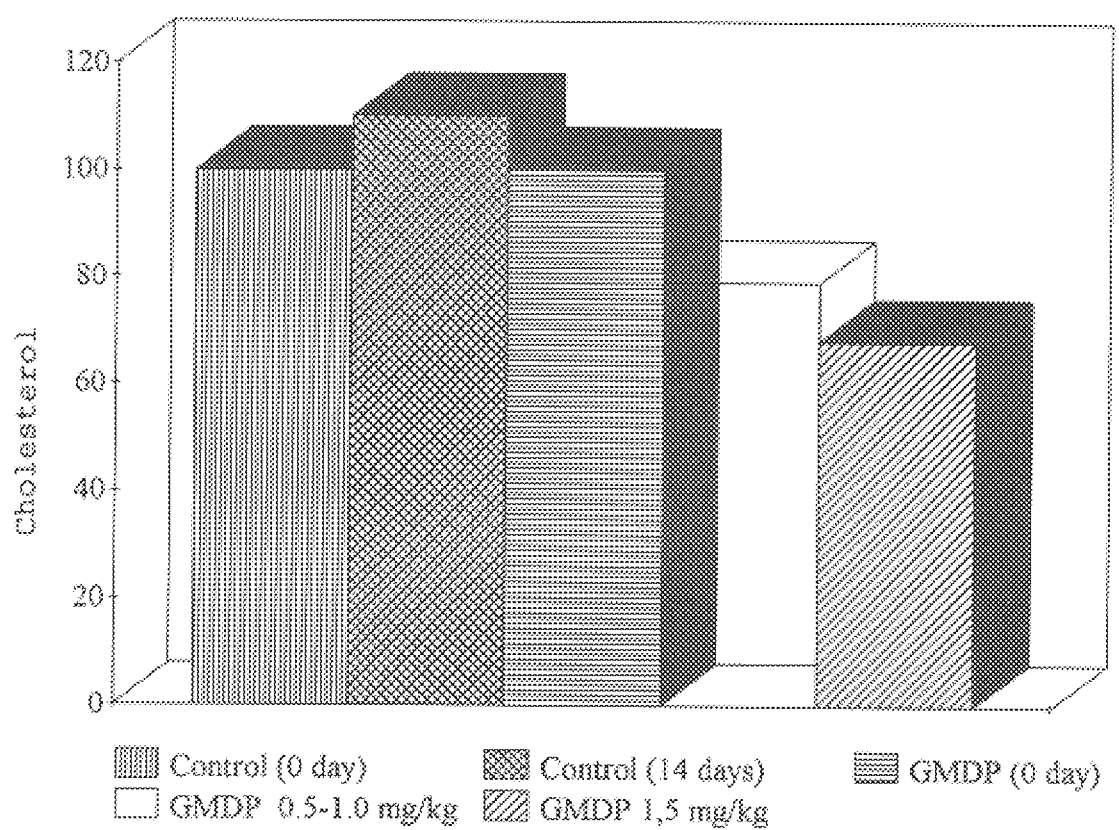
FIG. 10 Cholesterol level during tumor shock.

As used herein, the most preferred class of D-amino acid containing compounds for use in this invention is:

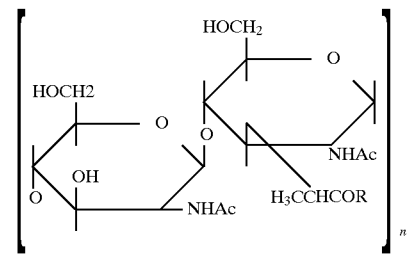

R represents the residue of aminoacid or linear peptides built up of from 2 to 8 amino acid residues, at least one residue being optionally substituted with a lipophilic group or D-isomer analogue.

Preferred position of this D-aminoacid residue is second, third from proximal end or second or third from distal end of a linear peptide. The most preferable position is second from proximal end. R preferably represents a di-or tri-peptide residue. The proximal residue is preferably that of L-amino acid and is selected from the group consisting of:
L-leucyl
L-isoleucyl
L-seryl
L-aminobutyryl
L-threonyl
L-tryptophanyl
L-lysyl
L-ornithyl
L-argynyl
L-histidil
L-ornithyl
L-cysteinyl
L-phenylalanyl
L-tyrosyl
L-arginyl
L-asparaginyl
L-prolyl
L-hydroxyprolyl
L-glutaminyl
L-aspartyl
L-methionyl
L-alanyl is most preferred.

The next amino acid from the proximal end of the peptide is preferably of the D-configuration. Most preferable D-isoglutamine and D-glutamate.

L-alanyl and L-lysyl are preferred for a third amino acid position from the proximal end of the peptide.

Most preferred class of D-amino acid containing compounds for use in this invention is wherein:

Most preferred dipeptides are L-Ala-D-isoGln and L-Ala-D-Glu.

One of the most preferred compounds in this invention which corresponds to the last formula is N-acetyl-D-glucosaminyl-(β1–4)-N-acetylmuramyl-L-alanyl-D-isoglutamine (GMDP) and N-acetyl-D-glucosaminyl-(β1–4)-N-acetylmuramyl-L-alanyl-D-glutamic acid (GMDP-A).

Other useful compounds which fall within the last formula are:

N-acetyl-D-glucosaminyl-(β1–4)-N-acetylmuramyl-L-alanyl-D-glutamine-n-butylester (GMDP-OBu),
N-acetyl-D-glucosaminyl-(β1–4)-N-acetylmutamyl-L-alanyl-D-isoglutaminyl-L-lysine(GMDP-Lys),
L-Threonyl-N-[N-Acetyl-D-glucosaminyl]-L-lysyl-D-prolyl-L-arginine.

Those compounds which are members of the most preferred class are N-aetyl-D-glucosaminylmuramyl-L-alanyl-D-isoglutamine, and N-acetyl-D-glusaminylmuramyl-L-alanyl-D-glutamine.

A further advantage of the preferred compounds of general formula mentioned above is that they are water soluble which facilitates their administration to the patients. We believe that the presence of D-isoglutamine in these compounds is crucial for expressing the biological activity of GMDP particularly its inhibition of TNF-α cytotoxicity.

Despite the classical knowledge that muramyl peptides (including GMDP) stimulate TNF-α production by macrophages and other cell types, we decided to use GMDP as a protector of all cells not only from toxic but also from pleiotropic effects of TNF-α. Successful exploitation of these newly discovered GMDP properties for the first time provided real opportunity to use one compound for the treatment of eventually all pathological conditions, where TNF-alpha is involved as a cytokine unifying the common mechanism of many diseases.

It is worthwhile to point out that very often these conditions look absolutely unrelated to each other. For example, from a conventional point of view there is a slight unity, if any, between pulmonary edema, cardiac allograft rejection, ischemic heart disease, preterm labor, toxicity of the pregnancy, left ventricular disfunction, myocarditis, cardiomyopathy, cachexia, acute respiratory distress syndrome, burn and tumor shock. Consequently, it at first may be hard to accept the fact of a common treatment for these different conditions. Yet it has been shown by applicant that in a variety of cell lines all these conditions can be treated according to the newly discovered phenomena of the inhibitory effects of GMDP over the cytotoxic nature of TNF-α.

This list is, however, given by way of example only and it should be understood that the present invention is of use in the treatment of any disease likely to be caused by pleiotropic effects of TNF-α.

Tumor shock is a deadly complication which occurs in the patients with terminate stage of cancer. Literally all cells, tissues, and organs of human body are experiencing permanent toxic effect of TNF-α, which is reflected in the elevation of all 5 LDH isoenzymes. Cachexia is a common result of it. In this situation, the task to protect all cells from TNF-α toxicity acquires vital importance and would allow to keep the patients alive and for the first time to treat tumor shock successfully.

In this respect, we intentionally neglected the opportunity to check the level of TNF-α because it does not reflect actual cytotoxic effects of TNF-α and can not be used as a reliable assay for the monitoring of the treatment. (See example 5).

The embodiment of the invention relating to the pharmaceutical composition varies with the mode of administration, which may be topical, oral, vaginal, rectal, and as a food supplement.

For topical administration, this composition comprises an effective amount of this compound in admixture with pharmaceutically acceptable nontoxic carrier. A suitable range of composition would be 10%–30% active ingredient. The concentration of D-compound in pharmaceutical compositions suitable for topical application will vary depending upon the particular activity used in conjunction with the condition and subject to be treated. Suitable carries include creams, ointments, lotions, emulsions and solutions.

The precise dosage for oral administration will be judged by the clinician or physician. However, in general, an average daily dosage would be in the range of from 1 mg to about 140 mg per day (or per tablet or other unit dose). It is likely, that a dosage range of from about 5 mg to about 70 mg per day (or per tablet or other unit dose) will be preferred and a daily dosage of around 10 to about 50 mg is considered to be optimal. For oral administration, these compositions contain an effective amount of this compound incorporated in a mixture with any of the usually employed excipients such as, for example, pharmaceuticals of mannitol, lactose, starch, talcum, cellulose, glucose, sucrose. The active ingredient comprises 65%–95% of such formulations. Such compositions takes the form of solutions, tablets, pills, capsules, sustained release formulations and the like.

For vaginal and rectal applications GMDP will be administered as solution which can be sprayed on the mucosa, or in solid suppositories which can be inserted one time per day.

The route of administration of the compound will be defined by specific clinical situation. However, oral administration will be the typical route. Vaginal and rectal route are important due to sensitivity of compounds to low stomach pH. In the critical condition it is also possible to administer the compounds parenterally. Moreover, the compounds can be infused through a catheter locally into the area of tissue necrosis or possible fibrosis.

In the following specific examples the results of standard bioassays are described.

EXAMPLE 1

TESTING OF THE HUMAN AMNIOTIC FLUID FOR THE PRESENCE OF GMDP.

Antibody capture assay (Antibodies: A laboratory Manual (E. Harlow and D. Lane, eds.), Cold Spring Harbor Laboratory, 1988) with antigen competition variation has been used to detect GMDP in human amniotic fluid. Highly specific mouse E6/1.2 anti-GMDP monoclonal antibody ($Ka=2\times10^9M^{-1}$) and GMDP conjugated to polyacrylamide backbone through amino group of lysine (GMDP-Lys-PAA) were obtained from Dr. Nesmeyanov, the Shemyakin and Ovchinnikov Institute of Bioorganic Chemistry, Russian Academy of Sciences, Moscow, Russia.

Briefly, GMDP-Lys-PAA or serial dilutions of human female milk in phosphate buffered saline (PBS) were adsorbed onto wells of microtiter plates for several hours. After washing with PBS, remaining binding sites were blocked by 1 h incubations with 200 μl PBS+3% bovine serum albumin (BSA). After washing with PBS 100 μl of E6/1.2 antibody, diluted 1:1,000 or 1:2,000 with PBS+1% BSA, were added. The incubation was carried out for 1 h at room temperature. Plates were washed with PBS and incubated for 1 h at room temperature with 100 μl/well of 1:1000 dilution of goat anti-mouse IgG antibody conjugated to horseradish peroxidase (HRP) in PBS+1% BSA. After washing 100 μl of OPD solution (1 mg/ml) in 20 mM sodium citrate buffer, pH 4.5, containing 0.03% $H_2O_2$ were added. The reaction was stopped 10–20 min later by adding 50 μl/well of 2.5M $H_2SO_4$. Optical density at 492 nm was measured.

Two different amounts of GMDP-Lys-PAA in PBS were adsorbed onto wells of microtiter plates (1 μg/well and 0.1

μg/well). Washing and blocking of remaining binding sites were performed as described above. Before adding to wells, 50 μl of antibody (E6/1.2m, IgG1(k) or mouse IgG) were incubated with 50 μl of an antigen (GMDP in PBS or series dilutions of the amniotic fluid in PBS) for 15 min. Further steps were as described above. Inhibition index (I,%) was calculated from: I=(1−Ao/A$_1$)×100, where Ao and A1 are optical densities of samples without or with inhibitor, respectively.

FIGS. 1A,B shows the inhibition of E6/1.2 antibody interaction with the adsorbed GMDP-Lys-PAA by GMDP itself. FIG. 2 shows that human amniotic fluid competitively inhibits the interaction of E6/1.2 antibody with GMDP-Lys-PAA.

EXAMPLE 2

THE LDH ASSAY OF THE INHIBITION OF TNF-α CYTOTOXICITY.

The following cell lines were used for this assay: A549 (human lung carcinoma cells), A431 (human breast cancer), L929 (mouse breast cancer).

All cells are available commercially from ATCC. They were maintained in DME medium supplemented with 10% FCS and glutamine in CO2 incubator.

Lactate dehydrogenase (LDH) assay

Cells were seeded into 35 mm Petry dishes and grown to 70% confluence. Then they were treated with human recombinant TNF-α (gift from Cetus Co.) in the concentration indicated in the figures.

In the cases where the cells were not spontaneously sensitive to TNF-α induced cytolysis cycloheximide (CHX), a powerful blocker of the protein synthesis, which sensitizes the cells to TNF-α action was used in concentrations of 25 μg/ml.

The mechanism of the action of CHX is unknown, but it does not effect the TNFR1 and TNFR2, but rather blocks the synthesis of proteolytic enzymes which will eventually destroy the compounds of the TNF-α death pathway and thus protect molecules which are sensitive to proteolytic degradation. It leads to accumulation of proteins and cells otherwise totally resistant to TNF-α acquired sensitivity.

Sixteen hours after the treatment 20 μl samples of cultured supernatants were removed and assayed for LDH release by the Cytotox 96 assay (Promega Biotech., Madison, Wis.) in accordance with the manufacturer's instructions.

This method is based on the fact that when cells are dying they are releasing LDH. These cells are given a substrate, which will produce a color reaction and in the presence of LDH the reaction visibly changes color.

The samples were assayed in triplicate on an EL340 Microplate reader (Bio Tech Instruments Inc.) at 490 nm wave length. The average of the three readings was plotted on the graphs (FIGS. 2,3,4).

EXAMPLE 3

INHIBITION OF THE EFFECTS OF TNF-α ON CONTRACTIVITY OF ADULT CARDIAC MYOCYTES.

Myocardial samples were obtained from organ donors, whose hearts were initially considered for cardiac transplantation but were subsequently deemed unsuitable for transplantation because of blood type or size incompatibility. Freshly isolated myocytes were treated for 60 minutes at 37° C. with single concentration of GMDP (5 μg/ml). Control cells were treated with single concentration of recombinant human TNF-α (Genzyme) that is known to produce negative inotropic effects in isolated cardiac myocytes (200 μ/ml). Cell motion was characterized with video edge detection as previously described in detail (17). Results were expressed as percentage change in cell length from resting values.

FIG. 6. shows that in comparison with control (open bar) cardiac myocytes (n=60), cells treated with TNF-α (closed bars; n=40 cells/group) developed a concentration-dependent decrease in cell shortening. Pretreatment with GMDP completely attenuated the effects of 200 μ/ml TNF alfa on cell shortening.

FIG. 7. shows a typical time-intensity curve for fluorescence brightness in isolated cardiac myocytes treated with GMDP (open circles) and with 200 μ/ml TNF-alpha (closed triangles). As shown, the peak level of intracellular fluorescence brightness was reduced strikingly for the cells treated with 200 μ/ml TNF-α. The insert of this figure, which depicts values obtained for group data (n=45 cells/group), shows that there was ~38% decrease in the percent change in peak intensity of fluorescence brightness for the TNF-α treated cells. Taken together, these figures demonstrate that GMDP inhibits negative inotropic effects of TNF-α in isolated cardiac myocytes.

EXAMPLE 4

THE PREVENTION OF THE TNF-α CYTOTOXICITY DURING TUMOR SHOCK.

27 patients with terminate stage of cancer participated in this study. The study group consisted of 19 females and 8 males between 14 and 59 years of age. 3 of them have had malignant brain tumors glioblastoma multiforme, 9 patients had breast carcinoma with massive metastasis to the liver or brain, one patient had intermediate stage lymphoma, one of them had stomach cancer with liver metastasis, three patients had hepatomas with lung metastasis, and two of them pancreatic cancer with liver metastasis.

All patients have received conventional treatment with chemotherapy and radiation. All of them suffered from cachexia and their blood test revealed a three to twelve fold increase LDH activity above normal reference range for all five LDH isoenzymes. Based on these findings tumor shock was diagnosed. Eight patients were vomiting and nauseous.

19 patients were given GMDP orally at dosage of 50 mg daily as a water solution for fourteen days. 8 patients received a placebo. None of the subjects experienced side effects.

Results were expressed as percentage change in LDH activity from pretreatment values. FIG. 8 shows that in all control patients LDH activity was increased approximately 10% during this time of observation. On the contrary, all treated patients have shown persisted decreasing of LDH activity by 68 %—with the lowest level achieved at the fourteenth day. During the follow up period overall clinical condition of all patients treated with GMDP was improved. Nausea and vomiting subsided in 7 patients who had these symptoms of tumor toxicity before treatment.

EXAMPLE 5

GMDP INHIBITS TNF-ALPHA EFFECTS ON LIPID METABOLISM.

In previous example 9 treated patients and 4 control patients have had also elevated level triglycerides and cholesterol 2–10 times above normal reference range.

Results were expressed as percentage change in both triglycerides and cholesterol level from pretreatment values.

FIG. 9 shows 82% decreasing for triglycerides concentration. In parallel, the control patient demonstrated statistically insignificant changes in the blood level of this lipid.

FIG. 10 shows 51% reduction of elevated cholesterol level in the patient treated with GMDP.

STATEMENT OF UTILITY

The method of the present invention is useful in the treatment and remediation of disease in humans and domestic animals.

It will be understood by those skilled in the art that the present invention has been described with reference to specific examples but other variation are possible without departing from the inventive concept. Accordingly, it is desired that the scope of the invention be determined only with reference to the appended claims.

What is claimed is:

1. A method for the inhibition of cytotoxic and pleiotropic effects of tumor necrosis factor-$\alpha$ (TNF-$\alpha$) in humans or domestically useful animals wherein TNF-$\alpha$ production has not been induced by lipopolysaccharide which comprises the step: administering to the subject an effective dose of about 0.5–1.5 mg/kg of body weight of N-acetyl-D-glucosaminyl ($\beta$-1-4)-N-Acetyl-muramyl-L-alanyl-D-isoglutamine (GMDP), which provides competitive inhibition of tumor necrosis factor receptor-1 and tumor necrosis factor receptor-2.

2. The method of claim 1 which further comprises a method for treating tumor shock.

3. The method of claim 1 which further comprises a method for treating burn shock.

4. The method of claim 1 wherein the inhibition of pleiotropic effects of TNF-$\alpha$ further comprises a method of inhibiting pleiotropic effects of TNF-$\alpha$ on lipoprotein lipase in vivo reduces blood lipids.

5. The method of claim 1 wherein the inhibition of the pleiotropic effects of TNF-$\alpha$ further comprises a method of treating massive tissue necrosis, proliferation of fibroblast, and epidermal cells, and a subsequent reduction in collagen production.

6. The method of claim 1 wherein the GMDP inhibition of the pleiotropic effect of TNF-alpha further comprises a method for decreasing cholesterol and triglycerides.

7. The method of claim 1 which further comprises a method for treating and reducing the symptoms of TNF-$\alpha$ induced cardiomyopathy, left ventricle disfunction and chronic heart failure.

8. The method of claim 1 which further comprises a method for treating and reducing the symptoms of stress-induced ischemic heart disease.

9. The method of claim 1 which further comprises a method for treating and reducing the symptoms of lung edema.

10. The method of claim 1 which further comprises a method for treating and reducing the symptoms of organ transplant rejection including cardiac allograft rejection.

11. The method of claim 1 which further comprises a method for treating and reducing the symptoms of TNF-$\alpha$ induced microvascular coagulation and myocardial infarction.

12. The method of claim 1 which further comprises a method for treating and reducing the symptoms of TNF-$\alpha$ induced myocarditis and myocardial reperfusion injury.

13. The method of claim 1 which further comprises a method of treating and reducing the symptoms of metabolic acidosis and hemoconcentration.

14. The method of claim 1 wherein TNF-$\alpha$ production, prior to administering GMDP, is not induced by lipopolysaccharide and further administering an effective amount of GMDP stimulates the production of TNF-$\alpha$.

15. A method to decrease lactate dehydrogenase (LDH) production in humans wherein LDH production is increased as a result of tumor necrosis factor-alpha (TNF-$\alpha$) cytotoxicity, comprising the step; administering to the human N-acetyl-D-glucosaminyl(B-1-4)-N-Acetyl-muramyl-L-alanyl-D-isoglutamine (GMDP) in an effective dose of about 0.5–1.5 mg/kg of body weight which administration provides a means for decreasing LDH production in said human.

16. The method of claim 15 wherein TNF-$\alpha$ production, prior to administering GMDP, is not induced by lipopolysaccharide and further administering an effective amount of GMDP stimulates the production of TNF-$\alpha$.

* * * * *